US006582472B2

(12) United States Patent
Hart

(10) Patent No.: US 6,582,472 B2
(45) Date of Patent: *Jun. 24, 2003

(54) KINETIC STENT

(75) Inventor: Charles C. Hart, Huntington Beach, CA (US)

(73) Assignee: Applied Medical Resources Corporation, Rancho Santa Margarita, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/806,337

(22) Filed: Feb. 26, 1997

(65) Prior Publication Data

US 2002/0062148 A1 May 23, 2002

(51) Int. Cl.[7] .................................................. A61F 2/06
(52) U.S. Cl. ...................... 623/23.7; 623/1.15; 623/1.2; 604/8
(58) Field of Search ................................ 606/198, 191, 606/195, 200; 623/1, 12, 1.2, 1.15, 23.7; 604/8

(56) References Cited

U.S. PATENT DOCUMENTS

| 3,996,938 A | * | 12/1976 | Clark ......................... 606/200 |
| 4,334,327 A | | 6/1982 | Lyman et al. ...................... 3/1 |
| 4,580,568 A | | 4/1986 | Gianturco ................... 128/345 |
| 4,643,716 A | | 2/1987 | Drach ........................... 604/8 |
| 4,655,771 A | * | 4/1987 | Wallsten ................. 604/282 X |
| 4,787,884 A | | 11/1988 | Goldberg ....................... 604/8 |
| 4,886,062 A | | 12/1989 | Wiktor ........................ 128/343 |
| 4,913,683 A | | 4/1990 | Gregory ......................... 604/8 |
| 4,931,037 A | | 6/1990 | Wetterman ..................... 604/8 |
| 4,957,479 A | | 9/1990 | Roemer .......................... 604/8 |
| 5,026,377 A | | 6/1991 | Burton et al. ................ 606/108 |
| 5,041,092 A | | 8/1991 | Barwick ...................... 604/104 |
| 5,041,093 A | * | 8/1991 | Chu ....................... 606/198 X |
| 5,059,139 A | * | 10/1991 | Zilber .................... 604/280 X |
| 5,078,720 A | | 1/1992 | Burton et al. ................ 606/108 |
| 5,116,309 A | | 5/1992 | Coll .............................. 604/8 |
| 5,222,971 A | * | 6/1993 | Willard et al. .............. 606/198 |
| 5,234,425 A | * | 8/1993 | Fogarty et al. ............. 606/198 |
| 5,246,445 A | * | 9/1993 | Yachia et al. ............... 623/1 X |

(List continued on next page.)

OTHER PUBLICATIONS

"Evaluation of A Chronic Indwelling Prototype Mesh Ureteral Stent In a Porcine Model", Owelny et al., Journal of Urology, vol. 163, No. 4, Supplement, Wednesday May 3, 2000, Section 1416.

*Primary Examiner*—Michael H. Thaler
(74) *Attorney, Agent, or Firm*—Richard L. Myers

(57) ABSTRACT

The disclosed stent is formed of an elongate, flexible duct having a very thin wall and a preformed diameter, length, and shape. The stent is constructed of a woven tubular structure of multiple strands or elements. The woven tubular structure is thermally set to a predetermined diameter and length, so that the "at rest" or natural condition of the tubular structure is predictable. A retention or holding member can be formed at one or both of the ends of the stent. This retention member can be reduced in diameter for insertion into the body passage. The woven tubular structure provides a path for fluids to flow in and around the stent, while a patent lumen is being developed. The woven tubular structure allows the stent to be extended or stretched over a guidewire or other noncompressive member, to thereby reduce the diameter of the stent for insertion of the stent into a body passage.

17 Claims, 11 Drawing Sheets

U.S. PATENT DOCUMENTS

| | | |
|---|---|---|
| 5,282,784 A | 2/1994 | Willard .......................... 604/8 |
| 5,306,294 A | 4/1994 | Winston et al. ................ 623/1 |
| 5,354,310 A * | 10/1994 | Garnic et al. ............... 606/198 |
| 5,364,340 A | 11/1994 | Coll .............................. 604/8 |
| 5,401,257 A | 3/1995 | Chevalier, Jr. et al. ..... 604/265 |
| 5,409,019 A | 4/1995 | Wilk ........................... 128/898 |
| 5,421,832 A * | 6/1995 | Lefebvre ................ 606/191 X |
| 5,466,242 A * | 11/1995 | Mori ........................... 606/198 |
| 5,476,505 A | 12/1995 | Limon ........................... 623/1 |
| 5,507,767 A | 4/1996 | Maeda et al. ................ 606/198 |
| 5,514,176 A * | 5/1996 | Bosley ........................... 623/1 |
| 5,540,701 A * | 7/1996 | Sharkey et al. ............. 606/198 |
| 5,575,818 A * | 11/1996 | Pinchuk .................. 606/195 X |
| 5,618,301 A * | 4/1997 | Hauenstein et al. ........ 606/198 |
| 5,645,559 A * | 7/1997 | Hachtman et al. .......... 606/198 |
| 5,667,486 A * | 9/1997 | Mikulich et al. ....... 606/195 X |

\* cited by examiner

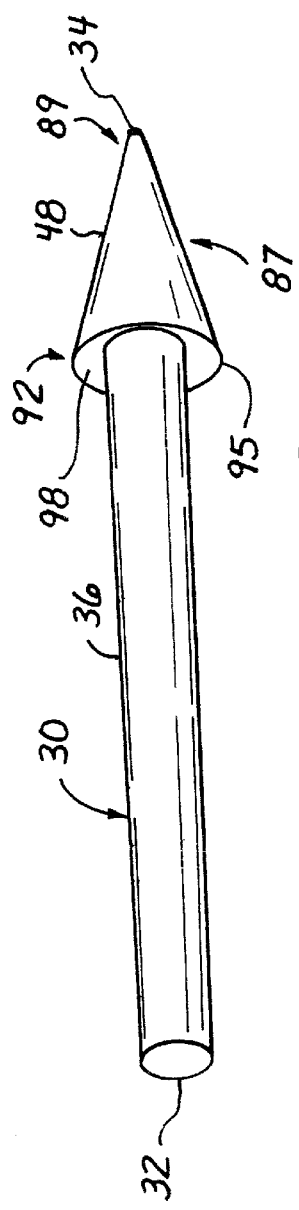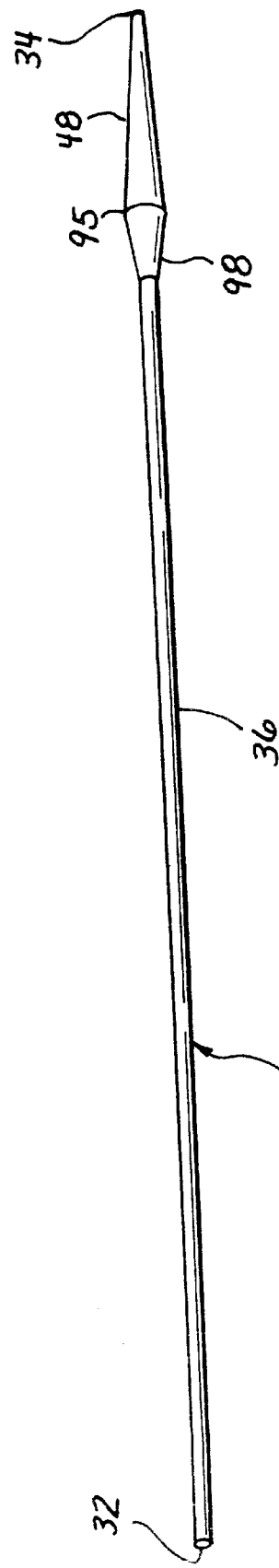

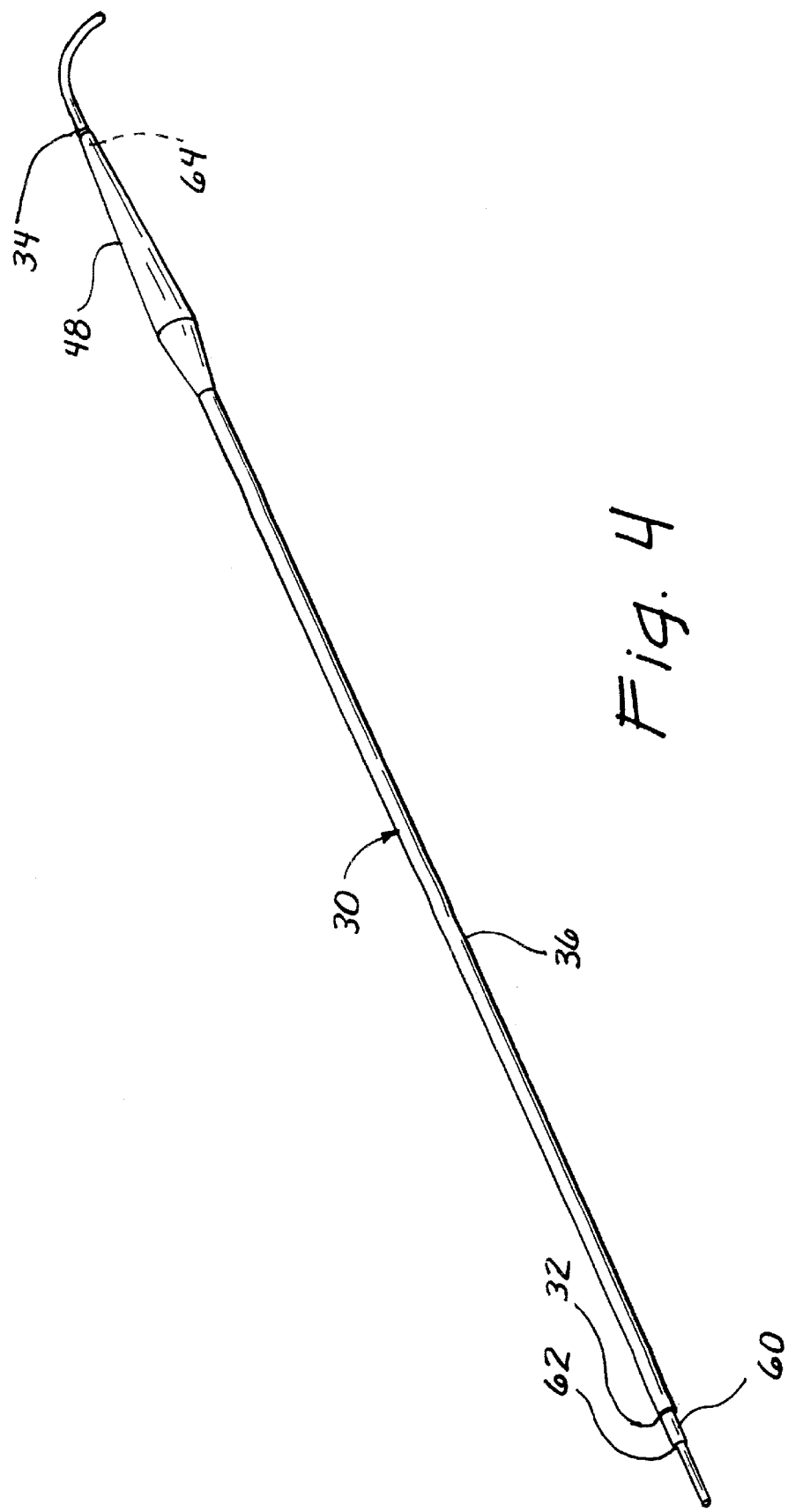

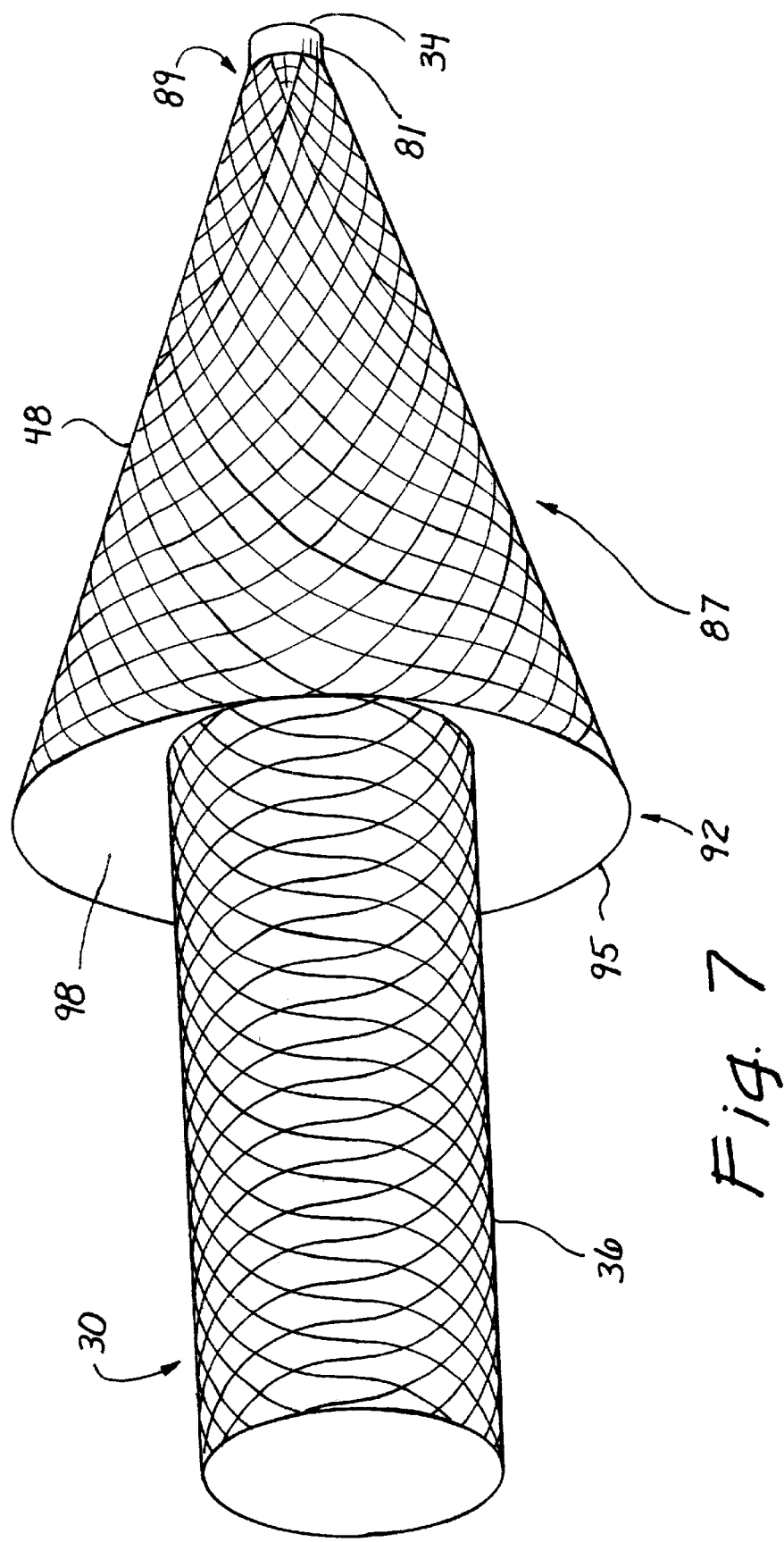

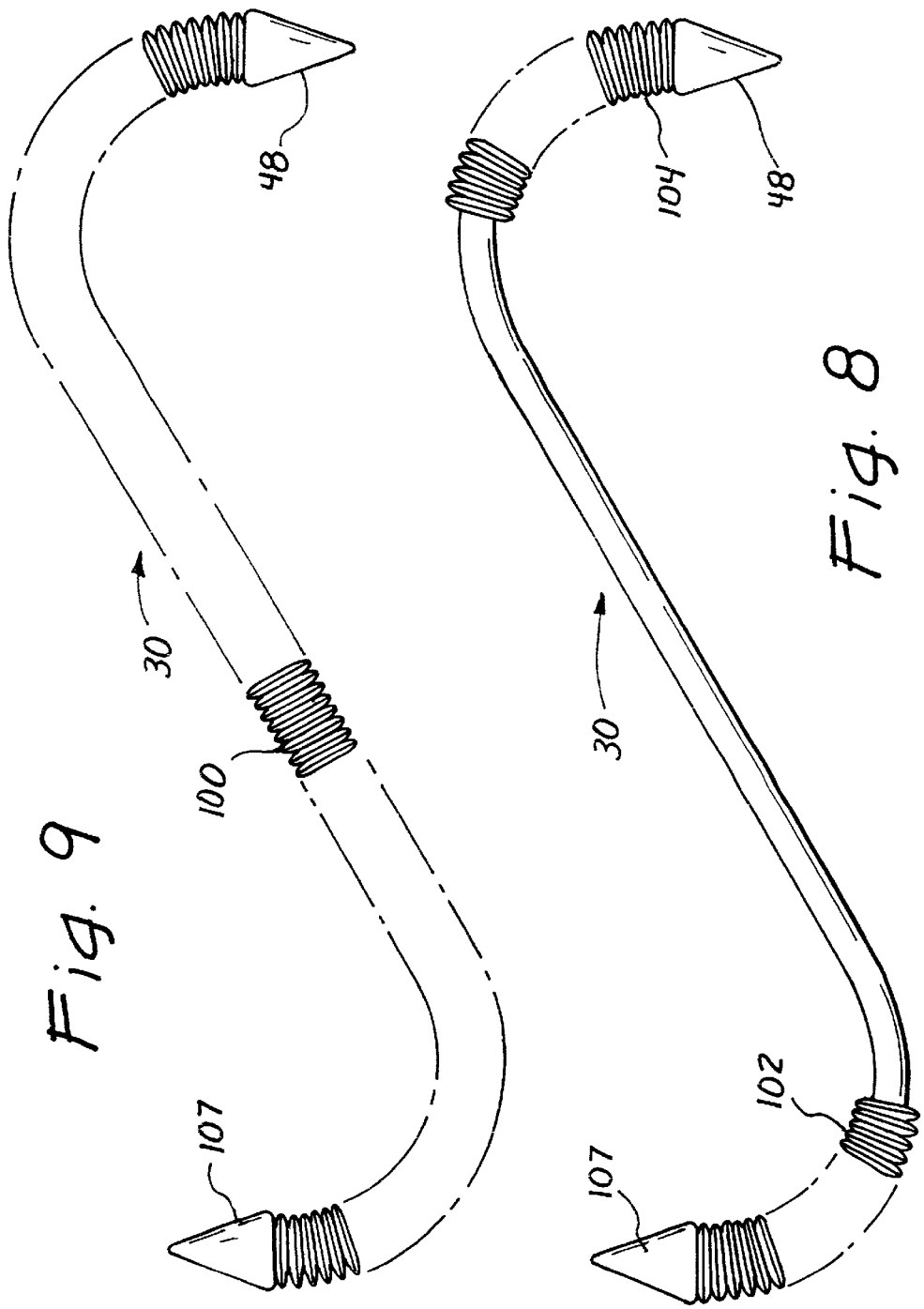

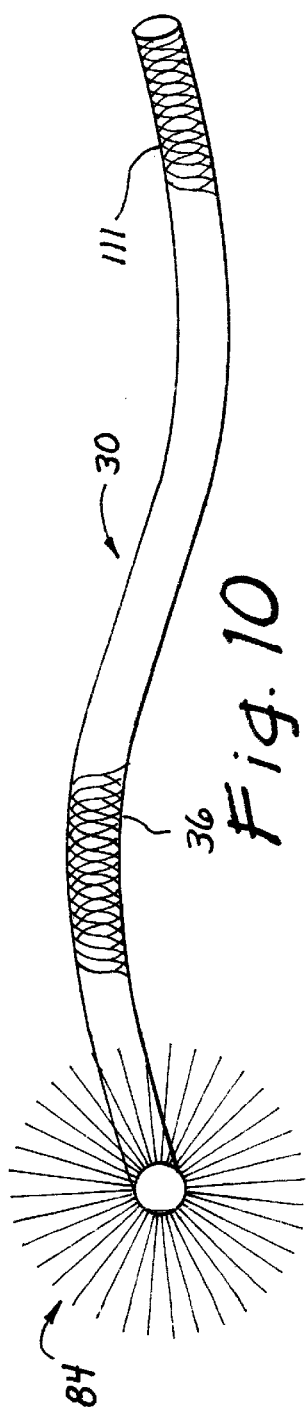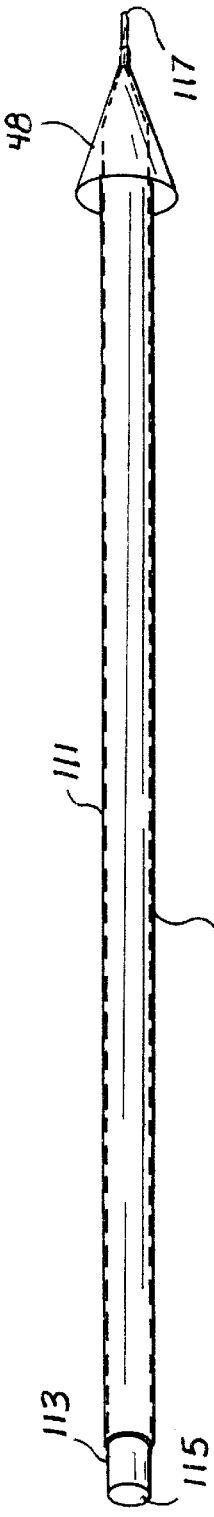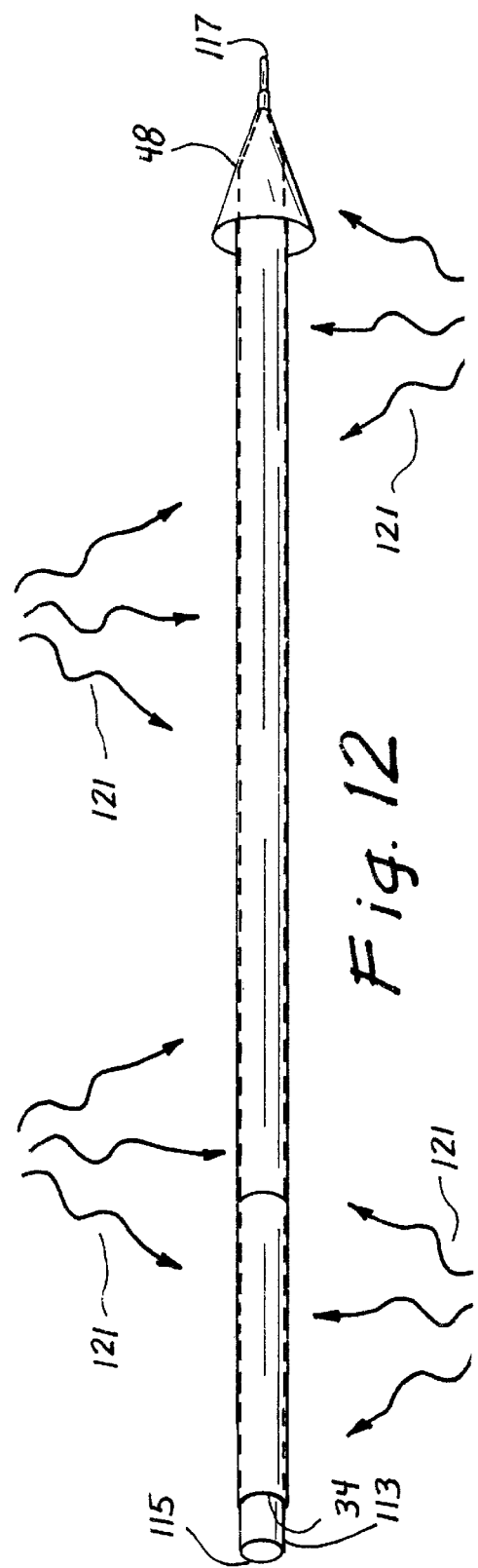

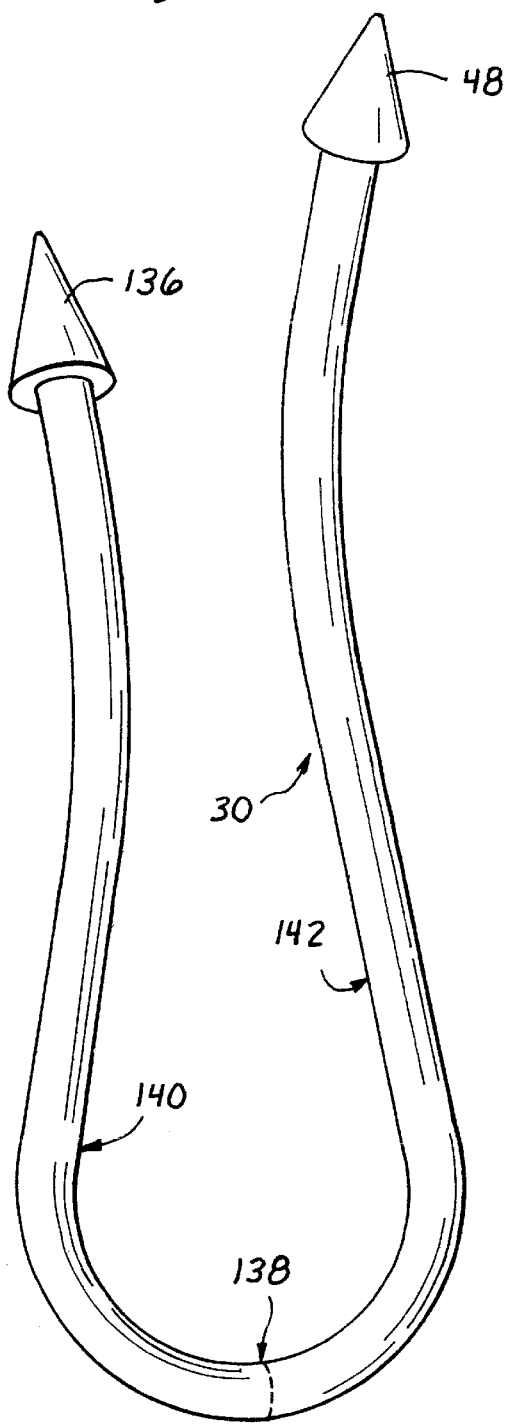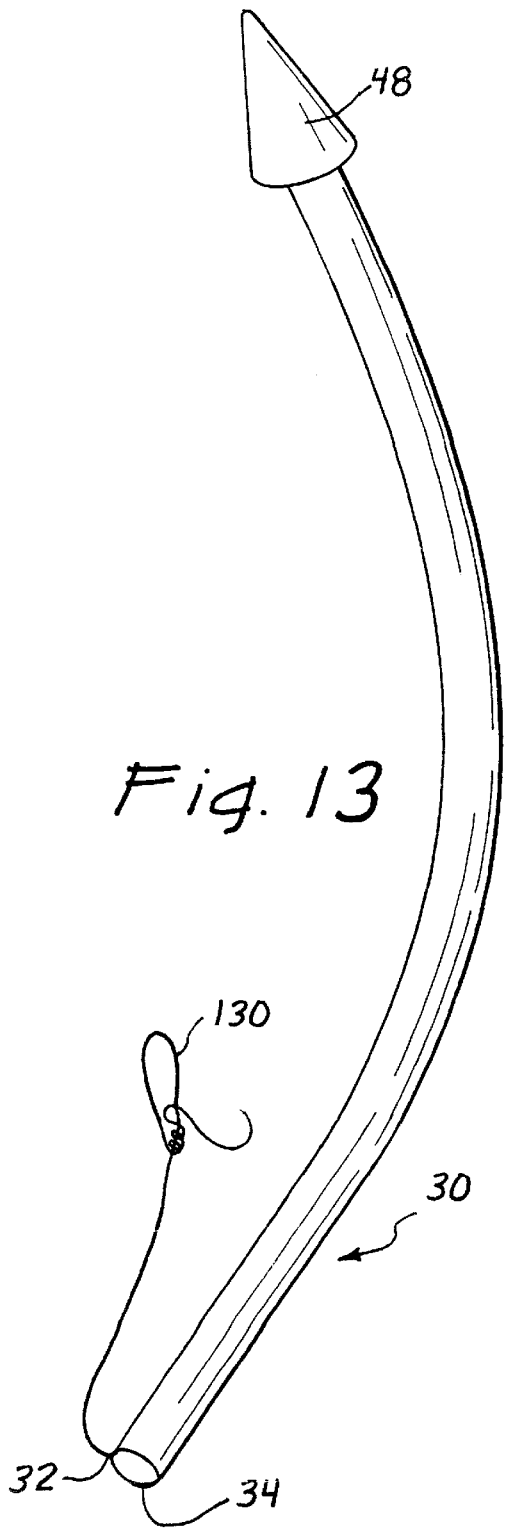

KINETIC STENT

BACKGROUND OF THE INVENTION

1. Field of the Invention

The present invention relates generally to stents for use in supporting and maintaining an open lumen within a body passage or vessel and, more particularly, to stents configurable between large and small diameters.

2. Description of Related Art

Tubular prosthesis, which are commonly referred to as stents, are used to reinforce or strengthen body passages or vessels. Occluded, collapsed, or compromised body passages, such as blood vessels, esophagus, tracheas, gastrointestinal tracts, bile ducts, ureters, and urethras, can all benefit from stents. These body passages can become occluded, collapsed, or compromised from disease, trauma, or from specific surgical procedures upon the wall of the body passage.

Prior art stents typically comprise a length of plastic tubular material, having a number of side holes disposed along the length of the plastic tubular material. U.S. Pat. Nos. 4,913,683, 4,643,716, 5,282,784, 4,957,479, 4,931,037, and 5,364,340 describe stents generally constructed in this manner. Each of these stents basically comprises a fixed diameter and, therefore, is nonresponsive to the specific diameter of a vessel.

A prosthesis or stent capable of expanding to appropriate diameters, along the length of the stent, can provide advantages over fixed-diameter stents. Self-expanding stents are disclosed in U.S. Pat. Nos. 5,026,377 and 5,078,720, both issued to Burton et al.; U.S. Pat. No. 5,019,085 issued to Hillstead; U.S. Pat. No. 4,969,458 issued to Wicktor; and U.S. Pat. No. 5,041,126 issued to Gianturco. These self-expanding stents are typically held in a contracted condition during insertion into the body passage or vessel and, after being positioned within the passage or vessel, released to expand fully. The stents of Wicktor and Gianturco comprise coiled or looped wires, which are unable to contact the entire surface of the interior wall of the affected vessel.

The Hillstead stent incorporates a multiple-loop wire structure, which suffers from the same deficiencies associated with the Wicktor and Gianturco stents. U.S. Pat. No. 5,507,767, issued to Maeda et al., discloses a self-expanding stent that employs a plurality of straight stainless steel wire sections, separating a plurality of bends, that may be adjusted and set to fit a particular anatomy or condition. U.S. Pat. No. 5,476,505 issued to Limon discloses a coiled stent for introduction into a body passage at a first diameter and subsequent expansion within the body passage to a second diameter. This coiled stent relies on a procedure for holding a coil in a tightly-wound condition during insertion of the coiled stent. U.S. Pat. No. 5,409,019 issued to Wilk discloses a stent, which surrounds a balloon, so that the collapsed balloon, upon expansion, can expand the stent. U.S. Pat. Nos. 5,078,720 and 5,026,377 issued to Burton et al. describe a combination of a self-expanding braided stent and an instrument for deployment or retraction of the stent. The instrument for deployment or retraction of the stent includes a tubular sleeve, which surrounds and compresses the braided stent. This surrounding tubular structure, requires that an additional wall thickness, corresponding to a thickness of the tubular sleeve, be added T o the device during placement. Consequently, a shortcoming of the Burton et al. invention is that the placement of the device is the time when the lowest profile or smallest diameter is required.

A need remains in the prior art for a prosthesis or stent which can be placed accurately into a low-profile or small-diameter condition and which can expand in diameter to a predictable size with a predictable pressure applied to an interior surface of the vessel wall. A need also exists in the prior art for a stent having a retention feature for maintaining the stent in a preferred position within the body passage. Additionally, a need exists in the prior art for a stent having a diameter, which is capable of responding and changing to the development of the lumen of the vessel or passage.

SUMMARY OF THE INVENTION

The stent of the present invention can be introduced into a body passage or vessel in a low profile or small diameter and, subsequently, expanded to a large diameter. The stent can be inserted into the body passage over a guidewire or small gauge catheter in the small diameter configuration. After the guidewire or small gauge catheter is removed, the stent is transformed into the large diameter configuration, which stimulates the reactive nature of the body passage to thereby develop or-maintain a patent lumen. The stent is able to provide maximum communication and flow of fluids from one surface of the stent to the other surface of the stent.

The stent of the present invention is formed of an elongate, flexible duct having a very thin wall and a pre-formed diameter, length, and shape. The stent is constructed of a woven tubular structure of multiple strands or elements. The woven tubular structure is thermally set to a predetermined diameter and length, so that the "at rest" or natural condition of the tubular structure is predictable. A retention or holding member can be formed at one or both of the ends of the stent. This retention member can be reduced in diameter for insertion into the body passage. The woven tubular structure provides a path for fluids to flow in and around the stent, while a patent lumen is being developed. The woven tubular structure allows the stent to be extended or stretched over a guidewire or other noncompressive member, to thereby reduce the diameter of the stent for insertion of the stent into a body passage.

According to one aspect of the present invention, a stent for use in a body passage includes an expandable tube having a proximal tube end, a distal tube end, and a lumen extending from the proximal tube end to the distal tube end. The expandable tube is configurable between a large-diameter relaxed state and a small-diameter tension state. The proximal tube end and the distal tube end are separated by a predetermined distance when the expandable tube is in the large-diameter relaxed state, and the proximal tube end and the distal tube end are separated by a second distance, which is larger than the predetermined distance, when the expandable tube is in the small-diameter tension state. A retention member is integrally formed with the expandable tube and is located just proximally of the distal tube end. The retention member has a large-diameter relaxed shape and a small-diameter tension shape, and has a retention-member diameter, in the large-diameter relaxed shape, which is greater than an expandable tube diameter of the expandable tube, when the expandable tube is in the large-diameter relaxed state. The stent further includes activating means adapted for increasing a distance between the proximal tube end and the distal tube end, to thereby change the expandable tube from the large-diameter relaxed state to the small-diameter tension state. The activating means is also adapted for changing the retention member from the large-diameter relaxed shape to the small-diameter tension shape, by increasing a distance between the proximal tube end and the distal tube end. The activating means includes a compression tube, which is adapted for fitting within the lumen and for contacting the distal tube end. The compression tube is further adapted for applying a distal force onto the distal tube end when a proximal force is applied to the proximal tube end. Application of both the distal force and the proximal force changes the expandable tube from the large-diameter relaxed state to the small-diameter tension state, and removal of both the distal force and the proximal force changes the expandable tube from the small-diameter tension state to the large-diameter relaxed state.

According to another aspect of the present invention, a stent includes a stent body formed of a braided material and an enlarged diameter retention member adjacent to the stent body and integrally formed with the stent body of the braided material. The large-diameter retention member is disposed near a distal end of the stent and comprises a cone shape. The stent further includes a rigid collar at a distal end of the cone-shaped retention member. The rigid collar defines an aperture. The stent includes a compression sleeve adapted for fitting within the stent body and for contacting the rigid collar. The stent is configurable into the insertion configuration by application of a distal force on the rigid collar by the compression sleeve, and is configurable into the stent configuration by removal of the distal force from the rigid collar. The stent further includes a guidewire adapted for fitting within the stent body and through the aperture. The retention member may also include a number of convolutions disposed on the stent body. These convolutions may cover a majority of the surface of the stent.

According to a further aspect of the present invention, a retention member for use in combination with a stent includes a tubular trunk formed of a braided material and a radially increasing portion formed in the braided material. The radially increasing portion is disposed adjacent to and integral with the tubular trunk, and extends substantially perpendicularly to a surface of the tubular trunk around a circumference of the tubular trunk. The retention member further includes a radially decreasing portion formed in the braided material and disposed adjacent to and integral with the tubular trunk. The radially increasing portion and the radially decreasing portion may comprise a cone shape, a convolution, or a combination thereof.

A method of accessing a body passage according to the present invention includes a step of converting a stent into a long-length, small-diameter insertion configuration by applying tension between a proximal end of the stent and a distal end of the stent, to thereby increase a distance between the proximal end of the stent and the distal end of the stent. The stent is then inserted into a body passage of a patient and moved through the body passage to a desired location. The stent is then converted into a small-length, large-diameter stent configuration by removing the tension, to thereby decrease the distance between the proximal end of the stent and the distal end of the stent.

A method of making a stent, which is transformable between a large-diameter configuration and a small-diameter configuration, begins with providing a woven tubular structure. The tubular structure is placed over a forming tool, which comprises a cylindrical body having a first diameter and a second diameter. Once the stent is formed, the stent will be transformable from the large-diameter configuration to the small-diameter configuration upon application from a compression sleeve of a distal force onto a distal end of the stent. The first diameter of the cylindrical body corresponds to the large-diameter configuration, and the second diameter of the cylindrical body is smaller than a diameter of the compression sleeve. After the stent is placed over the forming tool, the stent is irradiated with thermal energy, to thereby set a diameter of a portion of the woven tubular structure to the first diameter and to set a diameter of a distal end of the woven tubular structure to the second diameter. At a final step after the irradiating step, the resulting structure is removed from the forming tool. The forming tool may include a cone-shaped portion near a distal end of the cylindrical body, and the second diameter may correspond to a diameter of a guidewire. The irradiating step can be preceded by a step of folding a portion of the woven tubular structure, located proximally of the cone-shaped portion, proximally upon the forming tool to thereby form a retention member.

According to another method of the present invention, the forming tool comprises a cylindrical mandrel having both a first cone-shaped portion near a distal end of the cylindrical mandrel and a second cone-shaped portion near a proximal end of the cylindrical mandrel. The irradiating step is preceded by a first step of folding a portion of the woven tubular structure, located proximally of the first cone-shaped portion, proximally upon the mandrel to thereby form a first retention member, and a second step of folding a portion of the woven tubular structure, located distally of the second cone-shaped portion, distally upon the mandrel to thereby form a second retention member. The step of removing the resulting structure from the cylindrical mandrel is followed by a step of cutting the resulting structure in half, to thereby bisect the resulting structure into two stents.

The present invention, together with additional features and advantages thereof, may best be understood by reference to the following description taken in connection with the accompanying illustrative drawings.

BRIEF DESCRIPTION OF THE DRAWINGS

FIG. 2 is a side view of the stent in a radially expanded condition;

FIG. 3 is a side view of the stent in a radially compressed and longitudinally extended condition;

FIG. 4 is a side view of the stent of the present invention showing an introducer assembly;

FIG. 7 is an enlarged view of the retention member of the stent according to the present invention;

FIG. 8 is a view of one embodiment of the stent of the present invention having-convoluted sections at opposing ends of the stent body;

FIG. 9 is a view of one embodiment of the stent of the present invention having convolutions along the length of the stent body.

FIG. 10 is a view of a material suitable for the construction of the stent;

FIG. 11 is a view of a forming tool or mandrel being used to form the stent of the present invention;

FIG. 12 illustrates the use of a mandrel or forming tool and the use of heat to set the material of the stent to a preferred embodiment; FIG.

FIG. 13 is a view of one embodiment of the stent having a tether at one end;

FIG. 14 is a view of one embodiment of the stent of the present invention having a severable mid section;

DETAILED DESCRIPTION OF THE PRESENTLY PREFERRED EMBODIMENTS

Figure 1:
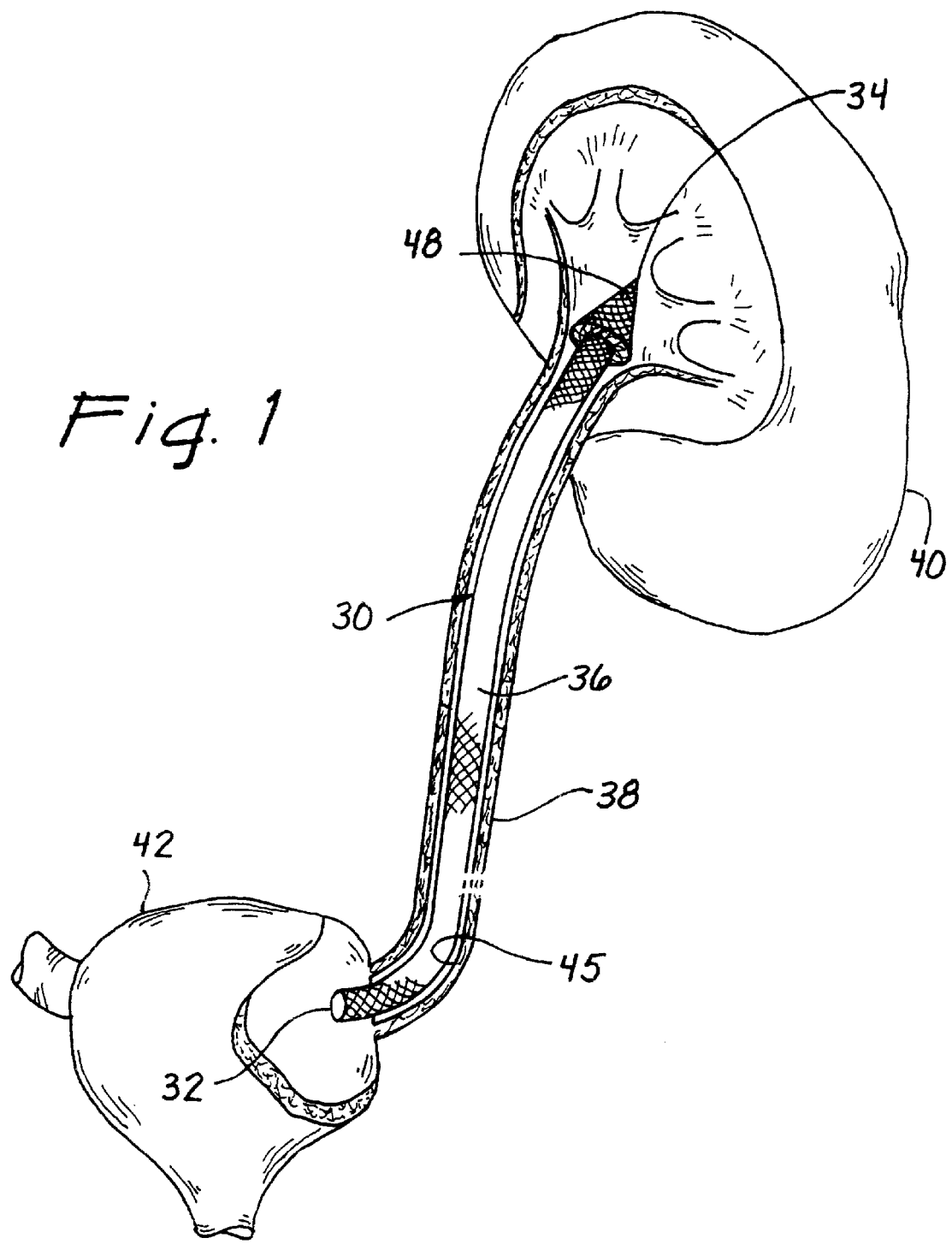
FIG. 1 is a schematic view of the stent of the present invention directed to pass through a ureter between a kidney and a urinary bladder.

Turning to FIG. 1, a stent or prosthesis 30 according to the presently preferred embodiment is illustrated having a proximal tube end 32 and a distal tube end 34. The stent body 36 is shown within a body passage or vessel 38, such as a ureter. The stent body 36 extends within the ureter 38 between a kidney 40 and a urinary bladder 42. The stent body 36 of the present invention is sized and configured to exert a compressive force against the interior surface 45 of the body passage 38. In the presently preferred embodiment, the stent 30 comprises a retention member 48 at the distal tube end 34. The stent 30 of the embodiment shown in FIG. 1 comprises a ureteral stent, which is adapted for developing or maintaining a patent lumen in the ureter 38 between the kidney 40 and the urinary bladder 42. The stent 30 facilitates passage of fluid in, through, and around the stent body 36 from the kidney 40 to the urinary bladder 42.

The stent of the present invention preferably comprises a woven material, which can be elongated and contracted. FIG. 2 is a side view of the stent 30 in a contracted, radially expanded condition. The condition illustrated in FIG. 2 corresponds to an "at rest" or natural condition of the stent 30. The lumen of the stent body 36 is fully developed along the length of the stent body 36, narrowing only at the distal tube end 34. The retention member 48, which forms a cuff or enlargement sized and configured to engage a portion of an organ or passage, has an enlarged diameter in the natural condition shown in FIG. 2. The retention member 48 assists in maintaining the stent 30 within the body passage 38, as illustrated in FIG. 1, for example.

FIG. 3 illustrates the stent 30 in a stretched, radially compressed and longitudinally extended condition. The stent body 36 is preferably reduced in diameter in order to facilitate placement of the stent 30 into a body passage 38. When the stent 30 is stretched along its axis, the diameters of the stent body 36 and the retention member 48 are significantly reduced to facilitate a low profile configuration for insertion into the body passage 38. As presently embodied, the stent 30 is placed into the low profile condition by application of a tensile force applied to both the proximal tube end 32 and the distal tube end 34.

As illustrated in FIG. 4, a compression sleeve 60, having a proximal end 62 and a distal end 64 (FIG. 5), can be inserted into a lumen of the stent 30. The compression sleeve 60 is preferably inserted into the lumen of the stent 30, until the distal end 64 of the compression sleeve 60 contacts the distal tube end 34 of the stent 30. After this placement, the proximal tube end 32 of the stent 30 can be drawn proximally, relative to the compression sleeve 60, to thereby facilitate elongation of the stent 30. In other words, since the distal end 64 of the compression sleeve 60 cannot pass through the narrow aperture of the distal tube end 34, movement of the proximal tube end 32 proximally will lengthen the stent 30. As the stent 30 increases in length, the diameter of the stent 30 decreases. The reduced diameter of the stent 30 facilitates a less-intrusive insertion of the assembly into a body passage 38.

A guidewire 70, having a proximal end 72 and a distal end 74, may be placed within the compression sleeve 60. The guidewire 70 provides a means for establishing a track, so that the stent 30 and compression sleeve 60 may be advanced along the guidewire 70 to a desired location within the body passage 38, with the stent 30 in an elongated configuration. After the stent 30 is moved to the desired location, the proximal tube end 32 of the stent 30 is released or relaxed, to thereby allow the proximal tube end 32 to move distally, resulting in an enlargement of the diameter of the stent 30. According to the presently preferred method of insertion, the guidewire 70 is placed within the body passage 38, and the stent 30 is then placed over the proximal end 72 of the guidewire 70. Next, the compression sleeve 60 is placed over the proximal end 72 of the guidewire 70 and into the stent body 36.

Figure 5:
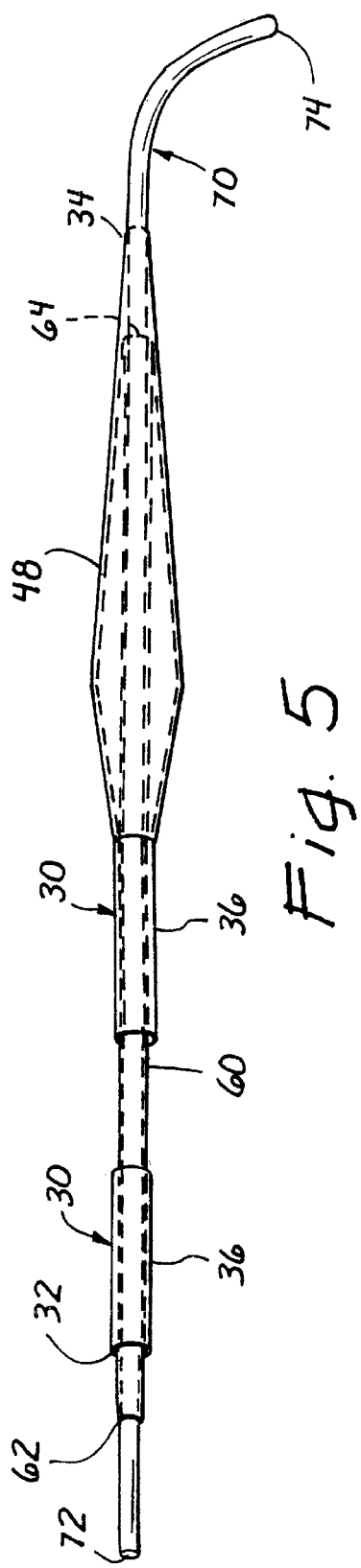
FIG. 5 is a cut away view of the stent positioned over an introducer assembly.
Figure 6:
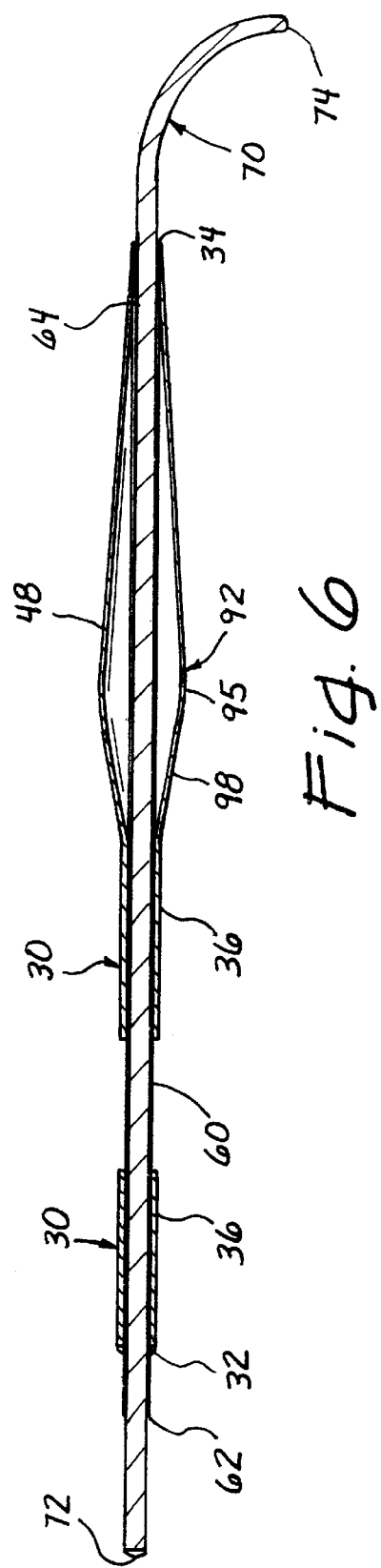
FIG. 6 is a cross-sectional view taken along the axis of both the stent and the introducer assembly.

FIG. 5 illustrates a cut-away view of the stent 30 positioned over both the compression sleeve 60 and the guidewire 70, and FIG. 6 illustrates a cross-sectional view of the assembly shown in FIG. 5. As illustrated in FIGS. 5 and 6, the compression sleeve 60 fits between the stent 30 and the guidewire 70. The opening at the distal end 34 of the stent 30 does not permit the distal end 64 of the compression sleeve 60 to pass through. This configuration permits the stent 30 to be stretched lengthwise, as the proximal end 32 of the stent 30 is extended proximally along the surface of the compression sleeve 60. At full extension, the profile of the stent 30 exceeds the outside diameter of the compression sleeve 60 by the thickness of the wall of the stent body 36. This extended/compressed relationship exists as long as a holding force is maintained between the proximal end 32 of the stent 30 and the compression sleeve 60. When this force is removed, the stent 30 assumes an "at rest" or expanded profile.

FIG. 7 illustrates an enlarged view of the retention member 48 of the presently preferred embodiment. The retention member 48 preferably comprises an enlarged diameter capable of engaging a portion within a vessel or organ, to thereby prevent the stent 30 from migrating or slipping from a desired position or location within the vessel or organ. The distal ring 81 of the retention member 48 is preferably sized and configured to prevent the compression sleeve 60 (FIG. 5) from passing therethrough. The distal ring 81 preferably comprises-a thermally fused or melted portion of material fibers 84 from which the stent 30 is woven. The distal ring 81, however, may be formed in other ways and/or comprise other materials. In the presently preferred embodiment, the retention member 48 comprises the shape of a cone 87 having a small diameter portion 89 distally located from a large diameter portion 92. The retention member 48 preferably comprises a substantially folded lip section 95 and a substantially folded angular portion 98 providing a transition between the stent body 36 and the retention member 48.

FIGS. 8 and 9 illustrate stents 30 having series of convolutions 100, 102, and 104 formed along the stent bodies 48. These convolutions 100, 102, 104 can operate to add strength to the retention members 48 and 107. The convolutions 100, 102, 104 also provide additional strength to the stent bodies 36 for resisting compression in much the same way as corrugated tubing resists kinking and compression. Additionally, the convolutions 100, 102, 104 assist in providing traction within the lumen of a body passage 38 and are sized and configured to be reduced in profile in the same manner as the stent body 36 by the application of traction or tension upon the stent body 36.

As illustrated in FIG. 10, the stent 30 is formed from an initial woven tubular structure 111, which preferably comprises a thermoplastic material or mesh. This construction begins by weaving or braiding a plurality of individual or groups of individual fibers or elements 84 into a tubular stent body 36. Desired characteristics may be developed within this construction for providing ratios of expansion to extension, as is known in the art.

After the woven tubular structure 111 is generated, the woven tubular structure 111 is placed onto a forming tool or mandrel 113 having a proximal end 115 and a distal end 117. The mandrel 113 serves as a form in setting the thermoplastic material of the woven tubular structure 111. In the presently preferred embodiment, the forming tool 113 comprises a first diameter near the proximal end 115 and a second diameter near the distal end 117. The first diameter represents the desired maximum deployed or expanded diameter of the stent body 36 when the stent body 36 is within a body passage or vessel 38, and the second diameter corresponds to the diameter of a conventional guidewire 70 (FIG. 6) but smaller in diameter than the diameter of the compressions sleeve 60 (FIG. 6).

The woven tubular structure 111 of the stent 30 is folded proximally upon the forming tool 113 to thereby form the retention member 48. As shown in FIG. 12, the forming tool 113 and the woven tubular structure 111 are next exposed to radiation 121 from a heat source or an oven preferably at a temperature sufficient to set the material of the woven tubular structure 111 to the preferred condition. In the presently preferred embodiment, the material comprises a thermoplastic, such as a polyester or nylon, since these materials allow for the development of a permanent, thermally set condition. Additionally, the distal tube end 34 and the distal ring 81 are preferably fused or melted to form a solid ring or collar which provides support for the compression sleeve 60. As a secondary operation, a proximal portion 123 of the stent body 36 may be coated with an elastomeric material to thereby provide stability at the proximal portion 123.

FIG. 13 illustrates a stent 30 having a tether 130 attached or formed at the proximal tube end 32 for assisting in the placement or the removal of the stent 30 from a body passage 38.

FIG. 14 illustrates a stent having a first retention member 48 and a second retention member 136 located at an end opposite from-the first retention member 48. The stent having the two retention members 48, 136 may be used as is or, alternatively, the stent may be cut at a preferred location 138 to form two individual stents 140 and 142.

Figure 15:
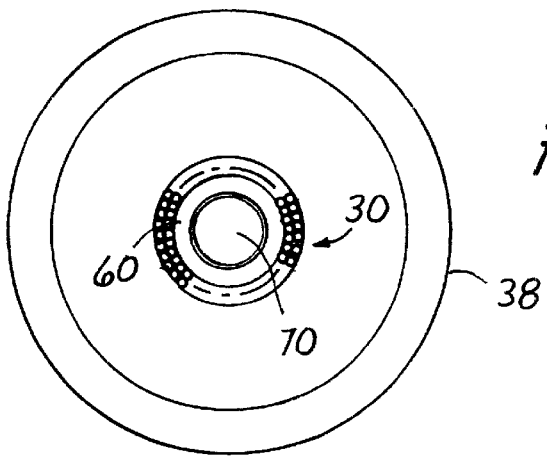
FIG. 15 is an end view of the stent in an elongated condition within a body passage or vessel.
Figure 16:
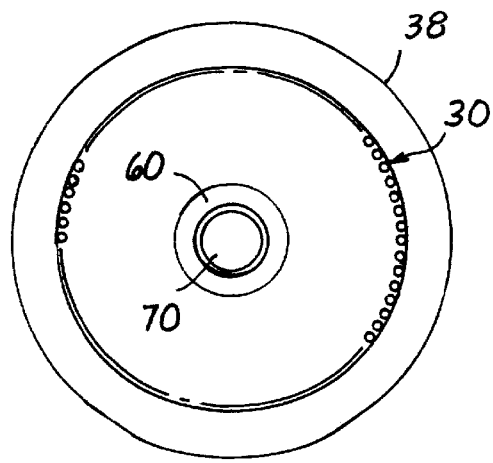
FIG. 16 is an end view of the stent in an expanded condition within a body passage or vessel.
Figure 17:
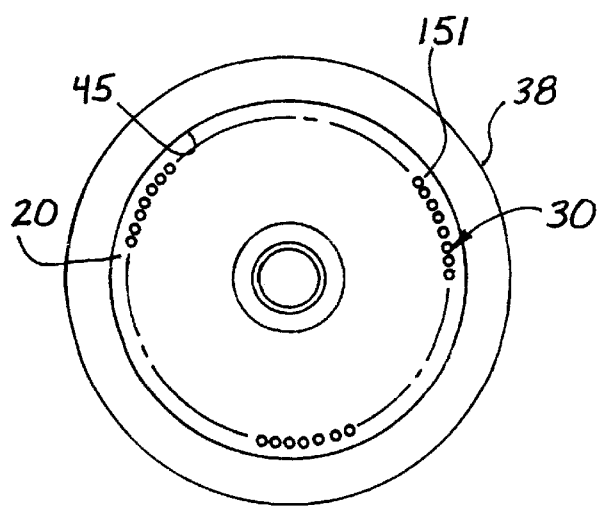
FIG. 17 is an illustration of the forces applied outwardly from the axis of the stent and against the wall structure of the body passage or vessel.

FIG. 15 illustrates an end view of the stent 30 of the presently preferred embodiment within a body passage 38. The stent 30 is illustrated in an extended, small diameter condition over both the compression sleeve 60 and the guidewire 70. FIGS. 16 and 17 illustrate the stent 30 in a large-diameter relaxed state. The guidewire 70 and the compression sleeve 60 may be removed at this time. The stent body 36 exerts a constant outward pressure 151 upon the interior surface 45 of the body passage 38. This outwardly directed radial pressure, along with the naturally occurring tendency for the intimal tissue to move away from a foreign body, combines to enlarge and/or maintain the lumen of the body passage 20.

Figure 18:
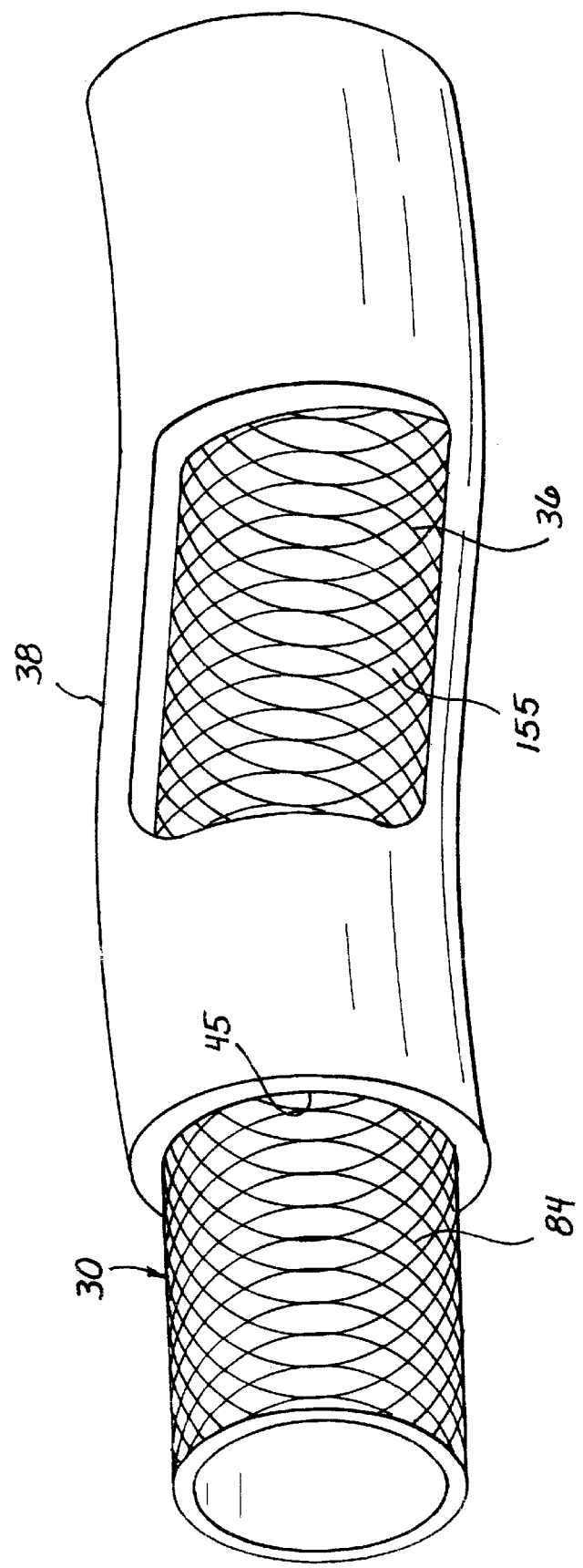
FIG. 18 is a cut-away view of the stent within a body passage or vessel in an expanded condition.

An enlarged view of a body passage 38 is provided in FIG. 18 with a stent 30 of the presently preferred embodiment fully extended within the lumen of the body passage 38. The individual fibers or groups of fibers 84 are spaced apart to thereby allow for the flow 155 of fluid through and around the stent body 36 as the stent body 36 applies outward pressure to the interior surface 45 of the body passage 38.

Figure 19:
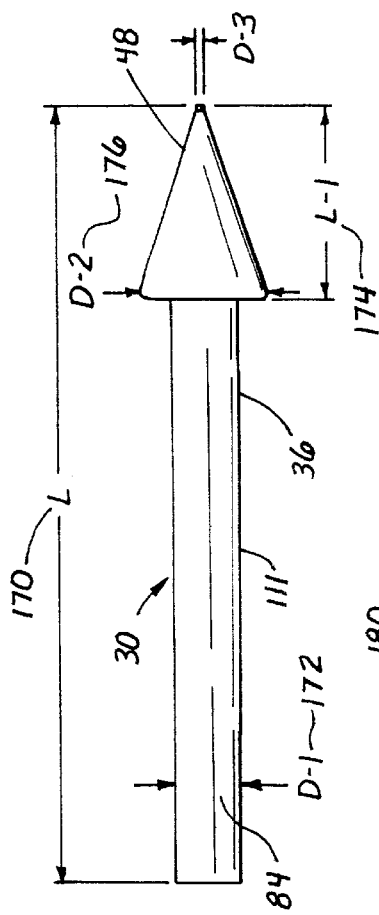
FIG. 19 illustrates the relative length to diameter feature in an expanded condition of the stent.
Figure 20:
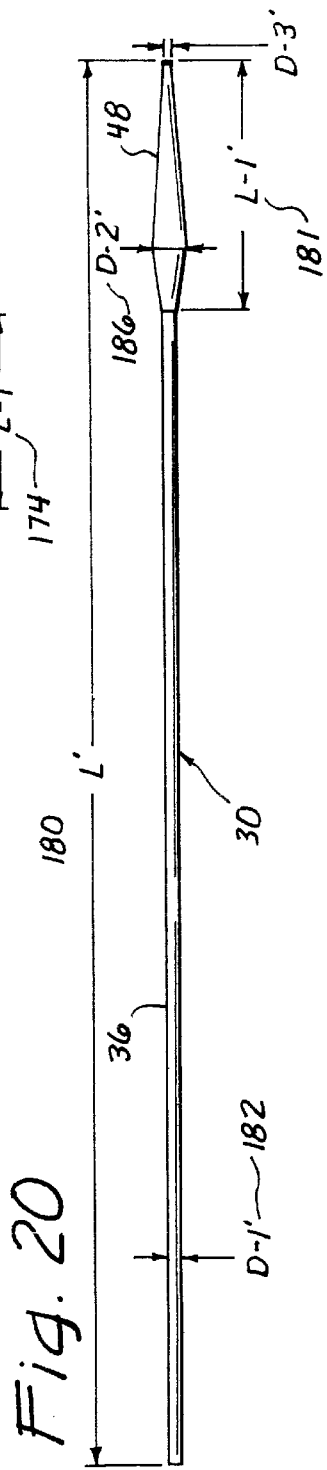
FIG. 20 illustrates the relative length to diameter feature in an extended condition of the stent.
Figure 21:
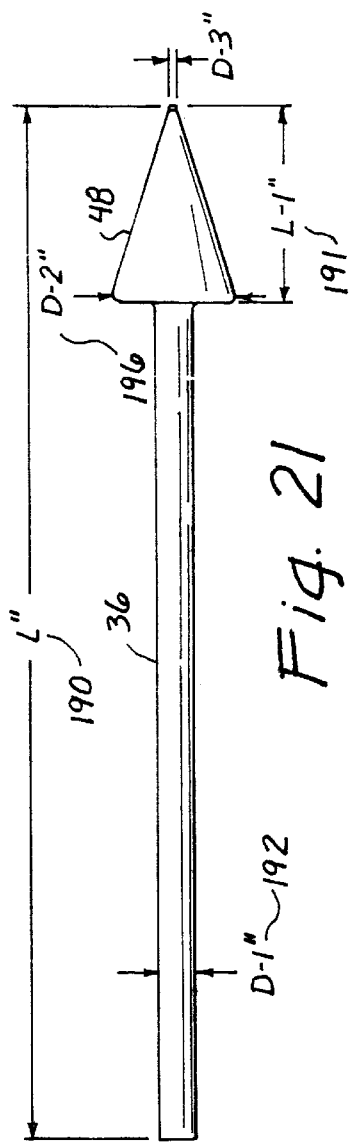
FIG. 21 illustrates the relative length to diameter feature in an intermediate condition of the stent.

The relationship between the length and the diameter of the stent 30 of the present invention is illustrated in FIGS. 19–21. The stent 30 in the "at rest" or natural, relaxed condition is illustrated in FIG. 19 with a fully expanded, maximum diameter 172. Due to the naturally occurring relationship of the fibers or elements 84 of a woven or braided tubular structure 111 (FIG. 10), a change in length 170 will accompany any change in diameter 172. Conversely, any change in length 170 precipitates a commensurate change in diameter 172. The present invention harnesses this relationship to facilitate the placement, maintenance, and removal of the stent 30. As presently embodied, the length 174 and the diameter 176 of the retention member 48 change somewhat proportionally to changes in the length 170 and diameter 172 of the stent body 36.

With reference to FIG. 20, as the stent 30 is stretched or extended in length 180, 181, the diameters 182 of the stent body 36 and the diameter 186 of the retention member 48 are both reduced. Upon removal or relaxation of the stretching or extending force, the stent 30 attempts to assume an original "thermally set" or natural condition within the body passage. Accordingly, the length 190 and the diameter 192 increase from the length 180 and the diameter 182 of FIG. 20, as illustrated in FIG. 21. Similarly, the length 191 and the diameter 196 of the retention member 48 increase. The increased diameters 192, 196 exert radially outwardly directed forces upon any resistive structure. As the diameters 192, 196 increase, the lumen within the body passage 38 will also increase, thereby facilitating further increases in the diameters 192, 196.

The intimal tissue of the body passage 38 responds to the presence of the braided material of the stent 30 by moving away from the braided material. In doing so, the lumen of the body passage 38 enlarges itself in response to the presence of the stent 30. As the lumen enlarges, the self-expanding stent 30 follows the inner surface of the body passage 38 and continues to expand. This, in turn, stimulates further enlargement of the lumen of the body passage 38. The expansion response development continues until a maximum lumen diameter is achieved. The expansion/response reaction is believed to be a reaction to the crossing members of the braided material and the motion of these crossing members within the body passage 38, especially when the body passage comprises a ureter. The expansion/response reaction may also be attributed to a general foreign body reaction within a body passage 38. In the particular case of a ureter, it is believed that the irritation from the braided or woven members causes the response. In this particular case, the braided or woven material of the stent 30 performs a majority of the work.

Although an exemplary embodiment of the invention has been shown and described, many other changes, modifications and substitutions, in addition to those set forth in the above paragraphs, may be made by one having ordinary skill in the art without necessarily departing from the spirit and scope of this invention.

What is claimed is:

1. A ureteral stent adapted for disposition in a ureter between a bladder and a kidney of a patient to facilitate dilation of the ureter to a desired diameter, comprising:
   a mesh body extending along an axis between a proximal end and a distal end, the body having a diameter and first properties for self-expanding to an ultimate diameter less than the desired diameter of the ureter so that the mesh body has a tendency to migrate within the ureter;
   the mesh body having an initial diameter less than the ultimate diameter for facilitating insertion of the ureteral stent into the ureter;
   the mesh body exhibiting the first properties for self-expansion between the initial diameter of the mesh body and the ultimate diameter of the mesh body;
   the mesh body having second properties for maintaining a radial space between the stent and the ureter to inhibit tissue in-growth to the mesh body when the stent is operably disposed in the ureter;
   a first anchor disposed at the distal end of the mesh body, the first anchor being configured for operative disposition in the kidney of the patient in order to inhibit migratation of the mesh body toward the bladder of the patient; and
   a second anchor disposed at the proximal end of the mesh body, the second anchor being configured for operative disposition in the bladder of the patient in order to inhibit migration of the mesh body toward the kidney of the patient.

2. The ureteral stent recited in claim 1 wherein the second anchor has a bulbous configuration and is sized and configured for operative disposition in the bladder of a patient.

3. A ureteral stent adapted for disposition in the ureter of a patient between a bladder and a kidney of the patient to facilitate dilation of the ureter to a desired diameter, comprising:
   a mesh body extending along an axis between a proximal end and a distal end the body having a diameter and first properties for self-expanding to an ultimate diameter less than the desired diameter of the ureter so that the mesh body has a tendency to migrate within the ureter;
   a first anchor being disposed at the first end of the mesh body and being sized and configured for operative disposition in the kidney of the patient, the first anchor inhibiting the migration of the mesh body in a first direction;
   a second anchor being disposed at the second end of the mesh body and being sized and configured for operative disposition in the bladder of the patient, the second anchor inhibiting the migration of the mesh body in a second direction opposite to the first direction;
   the mesh body having an initial diameter less than the ultimate diameter for facilitating insertion of the ureteral stent into the ureter;
   the mesh body exhibiting the first properties for self-expansion between the initial diameter and the ultimate diameter of the mesh body;
   the mesh body having second properties for maintaining a radial space between the stent and the ureter to inhibit tissue in-growth to the mesh body when the stent is operably disposed in the ureter; and
   at least one of the first anchor and the second anchor having a bulbous configuration of a cone with an apex and a base, the base being disposed between the mesh body and the apex of the cone.

4. A ureteral stent adapted for disposition in the ureter of a patient and adapted to extend completely from the bladder to the kidney of the patient to facilitate dilation of the ureter to a desired diameter, comprising:
   a mesh body extending along an axis between a proximal end and a distal end, the body having a diameter and first properties for self-expanding to an ultimate diameter less than the desired diameter of the ureter so that the mesh body has a tendency to migrate within the ureter;
   a first anchor having a bulbous configuration and being disposed at the first end of the mesh, the first anchor inhibiting the migration of the mesh body in a first direction, the first anchor sized and configured for operative disposition in the kidney of the patient; and
   a second anchor being disposed at the second end of the mesh body, the second anchor inhibiting the migration of the mesh body in a second direction opposite to the first direction, the second anchor being sized and configured for operative disposition in the bladder of the patient.

5. A ureteral stent adapted for disposition in the ureter of a patient and configured to exten completely from the bladder to the kidney of the patient to facilitate dilation of the ureter to a desired diameter, comprising:
   a mesh body extending along an axis between a proximal end and a distal end, the body having properties for self-expanding to a diameter not greater than an ultimate diameter less than the desired diameter of the ureter, so that the mesh body has a tendency to migrate within the ureter;
   a first anchor having a bulbous configuration at the first end of the mesh, the first anchor being sized and configured for operative disposition in the kidney of the patient in order to inhibit migration of the mesh body toward the bladder; and
   a second anchor disposed at the second end of the mesh body, and being sized and configured for operative disposition in the bladder of the patient in order to inhibit migration of the mesh body toward the kidney.

6. The ureteral stent recited in claim 3, 4 or 5, wherein: the mesh body has an initial diameter less than the ultimate diameter to facilitate insertion of the ureteral stent into the ureter.

7. The ureteral stent recited in claim 3, 4 or 5, wherein: the mesh body has properties for maintaining a radial space between the stent and the ureter to inhibit tissue in growth to the mesh body when the stent is operatively disposed in the ureter.

8. A ureteral stent adapted for disposition in the ureter of a patient, the ureter having an initial diameter and a desired ultimate diameter, the stent comprising:
   a wall having the general configuration of a cylinder with a first end, a second end, and a diameter, the wall having properties providing the diameter of the cylinder with variable characteristics;
   the wall having a first state wherein the diameter of the cylinder is less than about the initial diameter of the ureter in order to facilitate insertion of the stent into the ureter;

the wall having a second state wherein the cylinder has a maximum diameter sufficiently less than about the desired ultimate diameter of the ureter to facilitate creation of a space between the wall of the stent and the ureter in order to inhibit tissue ingrowth to the stent and to facilitate migration of the stent within the ureter;

a first anchor coupled to the first end of the wall and being adapted for disposition in the kidney to inhibit migration of the stent toward the bladder; and a second anchor coupled to the second end of the wall and being adapted for disposition in the bladder to inhibit migration of the stent toward the kidney.

9. The ureter stent recited in claim 8, wherein the wall comprises:

a woven mesh providing the diameter of the wall with the variable characteristics.

10. The ureteral stent recited in claim 9, wherein:

the cylinder of the wall has an axis; and the woven mesh in the first state of the wall is stretched axially to provide the cylinder with the diameter less than about the initial diameter of the ureter.

11. The ureteral stent recited in claim 9, wherein the woven mesh is formed of a thermoplastic material.

12. The ureteral stent recited in claim 11, wherein the thermoplastic material of the woven mesh is heatset to provide the cylinder with maximum diameter.

13. The ureteral stent recited in claim 8 wherein the wall has properties for self-expanding to automatically increase the diameter of the wall from the first state to the second state.

14. The ureteral stent recited in claim 8, wherein the space tends to facilitate migration of the stent within the ureter, and the stent further comprises:

at least one anchor coupled to the wall and being adapted for disposition in one of the kidneys and the bladder of the patient to inhibit the migration of the stent in the ureter.

15. A ureteral stent adapted for disposition in the ureter of a patient between a kidney and a bladder of the patient, in order to facilitate dilation of the ureter to a desired diameter, comprising:

a mesh body extending along an axis between a proximal end and a distal end, the body having a diameter and first properties for self-expanding to an ultimate diameter less than the desired diameter of the ureter so that the mesh body has a tendency to migrate within the ureter;

a first anchor having a bulbous configuration and being disposed at the distal end of the mesh body, the first anchor being adapted for operative disposition in the kidney of the patient in order to inhibit migration of the mesh body toward the bladder of the patient; and a second anchor being disposed at the proximal end of the mesh body, the second anchor being adapted for operative disposition in the bladder of the patient in order to inhibit migration of the mesh body toward the kidney of the patient.

16. The ureteral stent recited in claim 15 further comprising the mesh body having an initial diameter less than the ultimate diameter for facilitating insertion of the ureteral stent into the ureter; and the mesh body exhibiting the properties for self-expansion between the initial diameter of the mesh body and the ultimate diameter of the mesh body.

17. The ureteral stent recited in claim 16, wherein:

the mesh body has second properties for maintaining a radial space between the stent and the ureter to inhibit tissue in-growth to the mesh body when the stent is operably disposed in the ureter.

\* \* \* \* \*